(12) United States Patent
Simon et al.

(10) Patent No.: US 9,682,001 B1
(45) Date of Patent: Jun. 20, 2017

(54) WEARABLE BONE CONDUCTION DEVICE

(71) Applicant: Axiom Learning, Clyde Hill, WA (US)

(72) Inventors: Joanne Carullo Simon, Clyde Hill, WA (US); Stephenie Lee, San Francisco, CA (US)

(73) Assignee: Axiom Learning, Clyde Hill, WA (US)

( * ) Notice: Subject to any disclaimer, the term of this patent is extended or adjusted under 35 U.S.C. 154(b) by 0 days.

(21) Appl. No.: 15/162,968

(22) Filed: May 24, 2016

(51) Int. Cl.
*A61H 1/00* (2006.01)
*A61H 23/02* (2006.01)
*A61B 5/024* (2006.01)
*A61B 5/11* (2006.01)

(52) U.S. Cl.
CPC ......... *A61H 1/001* (2013.01); *A61B 5/02438* (2013.01); *A61B 5/11* (2013.01); *A61H 23/02* (2013.01); *A61H 23/0236* (2013.01); *A61H 2201/165* (2013.01); *A61H 2201/5002* (2013.01); *A61H 2201/5005* (2013.01); *A61H 2201/5048* (2013.01); *A61H 2205/065* (2013.01); *A61H 2230/065* (2013.01); *A61H 2230/625* (2013.01)

(58) Field of Classification Search
CPC .......... A61H 1/00; A61H 1/001; A61H 23/00; A61H 23/02; A61H 23/0218; A61H 23/0236; A61H 23/0245; A61H 23/0254; A61H 23/0263; A61H 2023/0209; A61H 2023/0272; A61H 2023/0281; A61H 2023/029; A61H 39/007; A61H 2201/165; A61H 2201/5048; A61H 2201/5002; A61H 2201/5005; A61H 2201/5064; A61H 2230/625; A61H 2230/60; A61H 2230/065; A61H 2230/06; A61M 2021/0022; A61M 2021/0027–2021/0038; A47C 21/006
See application file for complete search history.

(56) References Cited

U.S. PATENT DOCUMENTS 5,807,287 A * 9/1998 Cheng ................ A61H 23/0263
  5/915
8,801,591 B1 * 8/2014 Lasorso, Jr. ........... A61H 1/005
  600/28

(Continued)

*Primary Examiner* — Valerie L Woodward
(74) *Attorney, Agent, or Firm* — Wolf, Greenfield & Sacks, P.C.

(57) ABSTRACT

A wearable system including a controller and a plurality of wearable components configured to communicate with the controller is described. The controller performs a frequency analysis of music and sends control information to at least some of the wearable components based on the frequency analysis. The plurality of wearable components include at least one auditory stimulator configured to provide air conduction stimulation to the user, a plurality of vestibular stimulators configured to provide bone conduction stimulation to the user. The wearable system also includes at least one motion sensor configured to sense motion information, and at least one sympathetic arousal sensor configured to sense sympathetic arousal information of the user during stimulation by the plurality of vestibular stimulators. The controller is configured to adjust the control information based, at least in part, on the sensed motion information and/or the sensed sympathetic arousal information received from the sensors.

18 Claims, 10 Drawing Sheets

(56) References Cited

U.S. PATENT DOCUMENTS

| | | | |
|---|---|---|---|
| 2005/0154264 A1* | 7/2005 | Lecompte | A61B 5/4884 600/300 |
| 2007/0038164 A1* | 2/2007 | Afshar | A61H 23/0263 601/47 |
| 2012/0253236 A1* | 10/2012 | Snow | A61N 7/00 601/2 |
| 2014/0163439 A1* | 6/2014 | Uryash | A61B 8/08 601/47 |
| 2014/0276193 A1* | 9/2014 | Doochin | A61H 23/0245 600/552 |
| 2015/0305974 A1* | 10/2015 | Ehrenreich | A61H 23/0245 601/46 |
| 2015/0364059 A1* | 12/2015 | Marks | G09B 19/0038 482/9 |
| 2016/0058658 A1* | 3/2016 | Borras | H04M 1/72527 601/46 |

* cited by examiner

WEARABLE BONE CONDUCTION DEVICE

Sensory motor integration relates to the way in which the brain receives and processes sensory input to behave in a meaningful and consistent manner. People with poor sensory processing and integration are at risk of not receiving auditory and vestibular information that has important developmental value. A well-developed auditory and vestibular system allows for stronger bodily spatial awareness and an ability to use humans' finely tuned 360-degree sense to notice and protect themselves from incoming danger. Auditory input is also important for language and communication.

Some techniques for addressing deficits in sensory motor integration use sound therapies that focus on exposing people to various frequencies of sounds, typically with an emphasis on the higher frequencies, which elicit a brain response having a heightened state of alertness than the response to lower frequency sounds. In acclimating to these higher frequencies, individuals are able to use higher frequency sounds in their environment to more effectively access these states of heightened alertness. Some sound therapy programs also seek to remediate individuals with auditory input of a lower frequency. Lower frequency sounds induce a regulated, lowered state of alertness that can be described as "grounding" or "calming."

SUMMARY

Some embodiments are directed to providing body systems (e.g., the brain) with a sensory diet and input required to ensure that children and adults are able to regulate bodily rhythms, integrate sensory input, and allocate more energy towards tasks that are being consciously performed.

Some embodiments are directed to providing bone conduction stimulation to different parts of a person's body, allowing for adjustments for different therapeutic applications and an ability to deliver sound therapy that imitates the developmental progression of how body systems interact with sounds.

Some embodiments are directed to sensing motion using one or more motion sensors allowing for therapeutic movement activities to be performed with an improved precision not possible without the use of such sensors.

Some embodiments are directed to monitoring sympathetic arousal (e.g., heart rate) allowing for a preemptive assessment of sympathetic arousal of a user. Automatic adjustments to stimulation and/or therapeutic movement activities performed by the user may be made based on the monitored sympathetic arousal information.

Some embodiments are directed to a wearable system. The wearable system comprises a controller configured to communicate with each of a plurality of wearable components. The plurality of wearable components include at least one auditory stimulator configured to provide air conduction stimulation to the user in response to receiving first control information from the controller, wherein the air conduction stimulation is provided based, at least in part, on a frequency analysis of music processed by the controller. The plurality of wearable components further include a plurality of vestibular stimulators configured to provide bone conduction stimulation to the user in response to receiving second control information from the controller, wherein a first vestibular stimulator of the plurality of vestibular stimulators is integrated into a first wearable component of the wearable system configured to be worn in contact with a first portion of a user's body and a second vestibular stimulator of the plurality of vestibular stimulators is integrated into a second wearable component of the wearable system configured to be worn in contact with a second portion of the user's body. The plurality of wearable components further include at least one motion sensor integrated with the first wearable component and configured to sense motion information of the first portion of the user's body and provide the sensed motion information to the controller. The plurality of wearable components further include at least one sympathetic arousal sensor configured to sense sympathetic arousal information of the user during stimulation by the plurality of vestibular stimulators and to provide the sensed sympathetic arousal information to the controller. The controller is further configured to adjust the first control information and/or the second control information based, at least in part, on the sensed motion information and/or the sensed sympathetic arousal information.

Other embodiments are directed to a method of controlling a wearable system including a controller and a plurality of wearable components in communication with the controller, the plurality of wearable components including at least one auditory stimulator, a plurality of vestibular stimulators, at least one motion sensor, and at least one sympathetic arousal sensor. The method comprises performing, by the controller, a frequency analysis of music, receiving, by the at least one auditory stimulator, first control information from the controller, wherein the first control information is based, at least in part, on the frequency analysis of the music, providing, by the at least one auditory stimulator, air conduction stimulation to the user based, at least in part, on the first control information, receiving, by the plurality of vestibular stimulators, second control information from the controller, wherein the second control information is based, at least in part, on the frequency analysis of the music, and providing, by the plurality of vestibular stimulators, bone conduction stimulation to the user based, at least in part, on the second control information. The method further comprises sensing, by the at least one motion sensor, motion information of a portion of the user's body, transferring the sensed motion information from the at least one motion sensor to the controller, sensing, by the at least one sympathetic arousal sensor, sympathetic arousal information of the user during stimulation by the plurality of vestibular stimulators, transferring the sensed sympathetic arousal information from the at least one sympathetic arousal sensor to the controller, and adjusting, by the controller, the first control information and/or the second control information based, at least in part, on the sensed motion information and/or the sensed sympathetic arousal information.

Other embodiments are directed to a non-transitory computer readable medium encoded with a plurality of instructions that, when executed by at least one computer processor perform a method. The method comprises performing a frequency analysis of music, sending based, at least in part, on the frequency analysis of the music, first control information to at least one auditory stimulator configured to provide air conduction stimulation, sending, based, at least in part, on the frequency analysis of the music, second control information to each of a plurality of vestibular stimulators configured to provide bone conduction stimulation, receiving motion information of a portion of the user's body sensed by at least one motion sensor, receiving sympathetic arousal information of a user sensed by at least one sympathetic arousal sensor, and adjusting the first control information and/or the second control information based, at least in part, on the received motion information and/or the received sympathetic arousal information.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

BRIEF DESCRIPTION OF DRAWINGS

Various non-limiting embodiments of the technology will be described with reference to the following figures. It should be appreciated that the figures are not necessarily drawn to scale.

DETAILED DESCRIPTION

Figure 1:
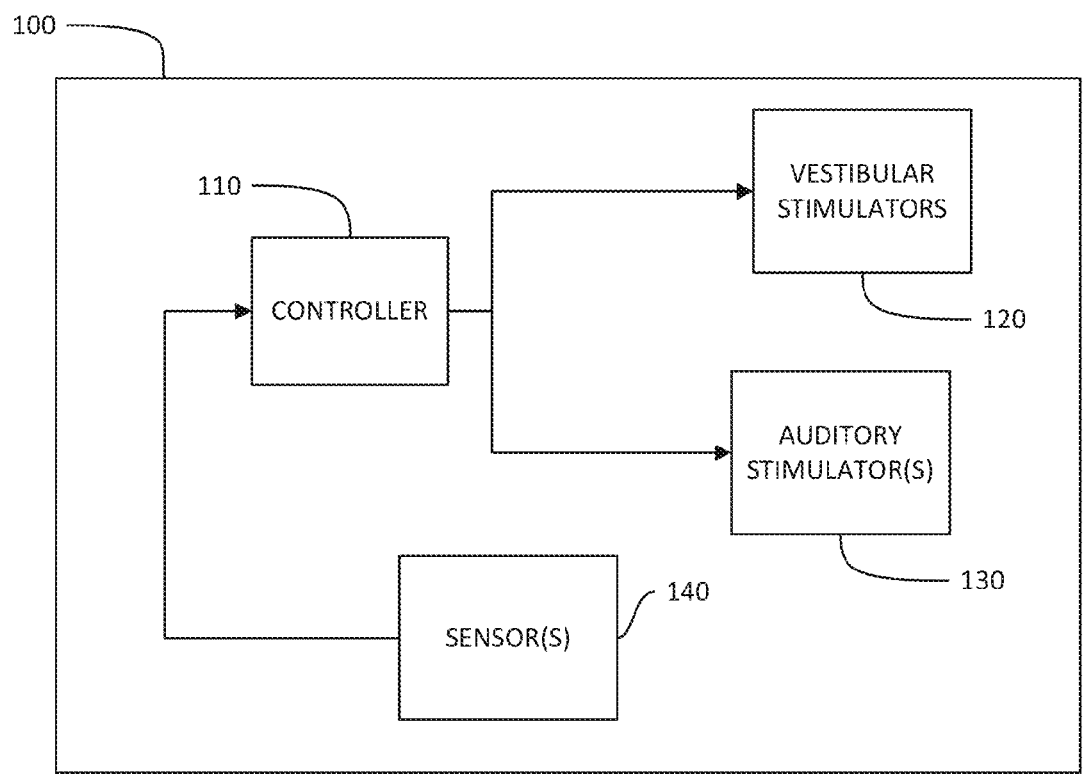
FIG. 1 shows a block diagram of components of a wearable system in accordance with some embodiments.

Therapeutic interventions for people with sensory motor integration difficulties are important to facilitate neurotypical cognitive and physical development. The inventors have recognized and appreciated that conventional sound-based therapies, often used to treat sensory motor disorders may be improved by providing coordinated auditory and vestibular stimulation. Some embodiments are directed to a wearable system that includes a plurality of wearable components configured to provide auditory stimulation and vestibular stimulation that more closely aligns with the developmental progression of how human systems interact with sounds.

In utero and during infancy as human bodies are gaining the muscle tone and posturing to stand upright, the primary source of auditory input is vibration-based sounds experienced through bones, also referred to herein as "bone conduction." In this period, the basic soothing techniques for parenting also involve the stimulation of a baby's vestibular system—from swinging the baby to the introduction of the humming of a fan or washing machine to the vibrations of a parent's voice as the baby is sung or spoken to. This type of vestibular input is important for body rhythm regulation and sensory motor integration important for higher levels of cognitive functioning later in development.

As development continues and humans become more upright, the auditory system acclimates to higher frequency air conduction as the primary input for sounds. One of the main sources of vestibular stimulation becomes experiencing one's own voice during vocal production. As such, while low frequency sounds are still experienced through parts of the body (e.g., feet) that connect with dense materials through which low frequency sounds travel, the head receives less and less direct bone conduction stimulation. Some embodiments are directed to a wearable device that provides bone conduction stimulation to multiple parts of the body, which may help an individual experience a fuller range of sounds. In some embodiments discussed in more detail below, the type of stimulation provided by the wearable system may be adjusted to distribute the bone conduction stimulation throughout multiple body systems in a manner more similar to that experienced in different phases of natural development.

Some therapeutic interventions to improve sensory motor integration include movement-based therapies that require an individual to perform movements of different parts of the body at specified timings. Many movement based therapies, including occupational therapy and physical therapy, rely on a trained professional's individual observational skills to evaluate the precision with which an individual is performing movements, the symmetry in the individual's movements, and the timing in the individual's movements. Because this evaluation is based on human observations, it is typically difficult to quantify incremental progress in the individual's movements. In some embodiments, the wearable system includes a plurality of motion sensors located at different parts of the body to track movements of the wearer of the system as they perform a movement-based activity. For example, some embodiments include motion sensors located at two or more of the head, wrists, ankles, and hips. Data from the motion sensors may be used to determine one or more of postural alignment during movements, the symmetry of the movements, excess movements that may be occurring, and timing of the individual's movements, resulting in a movement-tracking system with improved accuracy and having the ability to measure the progress in an individual's performance.

A well-regulated system is also important for optimal learning. Sympathetic arousal significantly disrupts bodily regulation. In some embodiments, the wearable system includes one or more sensors configured to track sympathetic arousal by monitoring, for example, the wearer's heart rate. Monitoring sympathetic arousal allows the wearer to be able to anticipate sensations of duress and develop self-awareness. Additionally, in some embodiments, sensed sympathetic arousal may be provided as feedback to adjust the level of bone conduction stimulation provided to one or more stimulators of the wearable system (e.g., in response to a heightened sympathetic arousal response to the physical exercises, sound therapy, and vestibular therapy).

A wearable system in accordance with some embodiments provides auditory and vestibular therapy to the wearer, while also being capable of tracking the posturing and alignment of the body and sympathetic system arousal. Such a system may be capable of analyzing and understanding the wearer's stress system activation and the accuracy of therapeutic movements. Combining auditory and vestibular therapy with visual-motor exercises that support the development of stronger movement differentiation and improved interhemispheric integration increases the rate at which body systems can benefit from therapies for individuals with sensory motor integration deficiencies.

FIG. 1 illustrates a schematic block diagram of a wearable system 100 in accordance with some embodiments. Wearable system 100 includes controller 110 configured to control the operation of one or more vestibular stimulators 120 and one or more auditory stimulators 130 that together are configured to provide therapy for individuals with sensory motor integration deficits. In some embodiments, controller 110 is implemented as an application executing on a computing device such as a smartphone or laptop computer. In other embodiments, controller 110 is implemented as a special-purpose processing circuitry (e.g., an ASIC or FPGA) that may be programmed to provide one or more control functions, example of which are described herein. When implemented as an application on a computing device, controller 110 may be configured to display a user interface on the computing device to enable a user wearing the system to select one or more control settings, examples of which are described in more detail below.

Wearable system 100 also includes a plurality of vestibular stimulators 120, each of which is configured to provide bone conduction stimulation to a different part of the body in response to control information received from controller 110. In one implementation, described in more detail below, wearable system 100 includes six vestibular sensors located at the head, waist, right wrist, left wrist, right ankle, and left ankle. Each of the vestibular stimulators 120 may be individually controllable by controller 110 to provide vestibular stimulation of the same or different intensities and/or frequencies at the part of the body over which the stimulator is placed. In some embodiments, vestibular stimulators 120 are implemented as vibrating bodies configured to vibrate at a particular amplitude and timing specified in control information received from the controller 110.

Wearable system 100 also includes one or more auditory stimulators 130, each of which is configured to provide auditory stimulation to the user of the wearable system 100 in response to control information received from controller 110. In some embodiments, auditory stimulator(s) 130 are implemented as speakers in headphones worn by a user of wearable system 100.

Wearable system 100 also includes one or more sensors configured to provide feedback about a state of the user to controller 110. In response to receiving the feedback, controller 110 may be configured to modify the control information sent to at least one of the vestibular stimulators 120 and/or auditory stimulators 130. Additionally or alternatively to modifying the stimulation control information, controller 110 may be configured to output an indication of the received feedback to the user (e.g., via a user interface on a computing device, such as a smartphone). In some embodiments, the feedback from the sensor(s) may be stored by at least one storage device in communication with controller 110.

Figure 2:
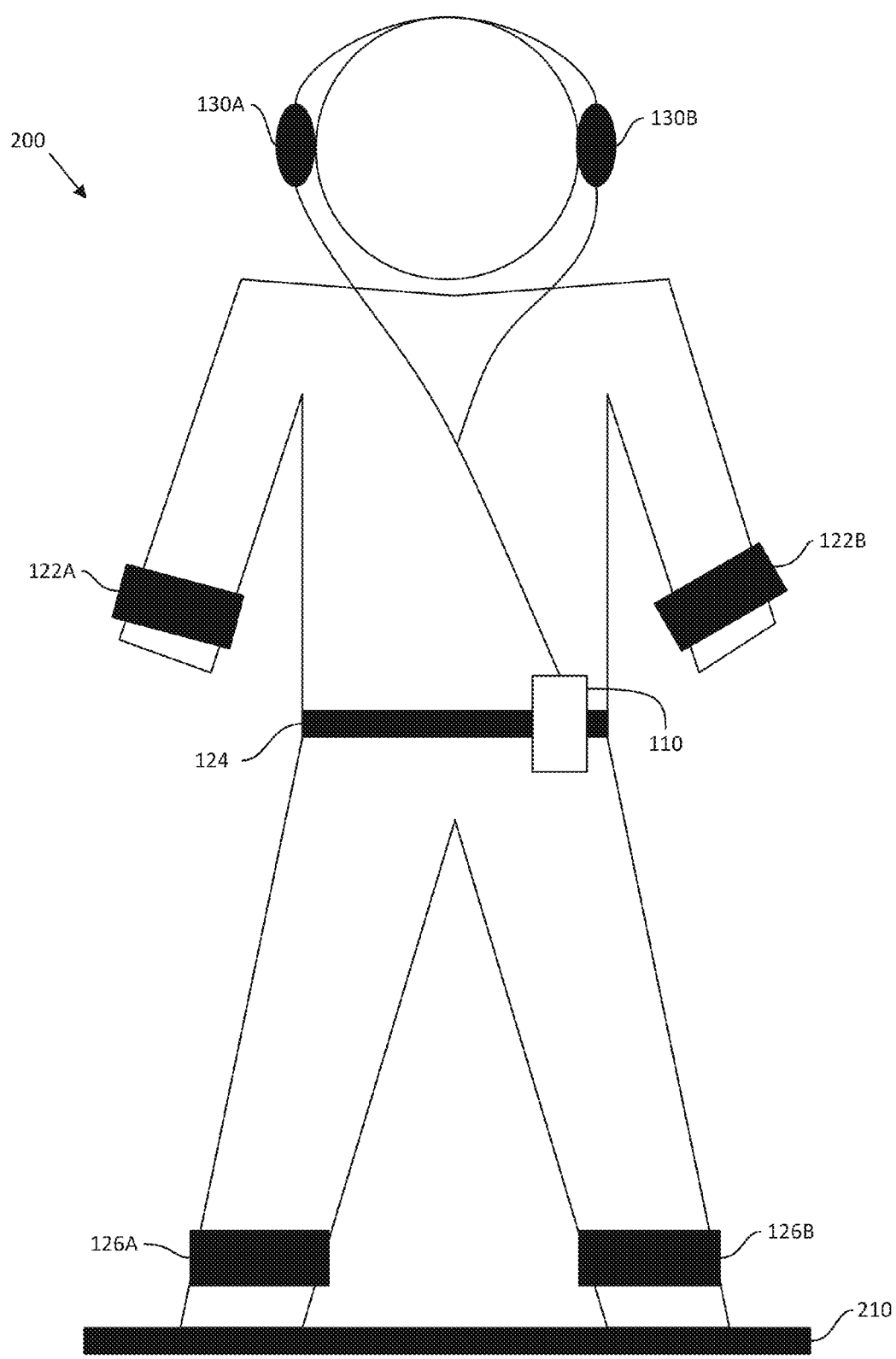
FIG. 2 schematically illustrates components of a wearable system worn by a user in accordance with some embodiments.

FIG. 2 illustrates a schematic diagram of a user wearing components of a wearable system 200. A wearable system in accordance with some embodiments is configured to transmit sound therapeutically to a wearer using auditory and vestibular stimulators, to sense and track data regarding movements being performed by the wearer, and to sense and use data regarding the user's sympathetic arousal to adjust characteristics of the stimulation provided to the user. The placement of the wearable components of the wearable system may be selected to correspond with parts of the human skeletal structure that are the receptors for vibratory input and may be good indicators for body posturing.

As shown, wearable system 200 includes controller 110. Controller 110 may be implemented, at least in part, as an application executing on a portable computing device, such as a smartphone. In addition to controlling the vestibular and auditory stimulators of the wearable system, the portable computing device may include other functionality including, but not limited to, playing and/or processing music files. In some embodiments, controller 110 is configured to process music files played by the portable computing device and information obtained by processing the music files may be used to determine control information transmitted from the controller to the vestibular and auditory stimulators. Controller 110 may communicate with the vestibular and auditory stimulators using any suitable wired or wireless connection. In some embodiments, controller 110 communicates with the stimulators using Bluetooth or another suitable wireless communication technology.

As shown, wearable system 200 includes a pair of auditory stimulators 130A, 130B implemented as speakers in headphones connected to controller 110 via a wired connection. It should be appreciated that information may alternatively be communicated between controller 110 and the auditory stimulators 130A, 130B using wireless communication or any combination of wired or wireless communication.

In some embodiments, one or more vestibular stimulators may be integrated with or located near the auditory stimulators 130A, 130B to provide bone conduction stimulation to portions of the head. For example, the headphones including auditory stimulators 130A and 130B may also include one or more vestibular stimulators (not shown) controllable by controller 110. The vestibular stimulators may be implemented in some embodiments as one or more vibrating bodies or panels that vibrate in one or more axes to provide bone conduction stimulation to a body region adjacent to the vestibular stimulator.

Wearable system 200 also includes a plurality of vestibular stimulators configured to be worn by a user at particular locations on the user's body. For example, the wearable system may include wrist stimulators 122A, 122B, hip stimulator 124, and ankle stimulators 126A, 126B. Each of the vestibular stimulators may be configured to receive control information from controller 110 and to provide bone conduction stimulation to a part of the user's body over which the stimulator is placed in response to receiving the control information from the controller.

Wrist stimulators 122A and 122B are shown in wearable system 200 as being incorporated into wristbands (e.g., sweat bands) that can be worn by a user to provide vestibular stimulation to the user's wrists. In some embodiments, wrist stimulators 122A and 122B may be implemented as gloves or as a portion of another article of wearable clothing such as the sleeve of a shirt or jacket. Components of a wrist stimulator that may be used in wearable system 200 in accordance with some embodiments, are discussed in more detail below, in connection with FIG. 3.

Hip stimulator 124 is shown in wearable system 200 as a belt worn around the hip area of user, with the belt including one or more vestibular stimulators integrated therein. Another article of clothing, such as the waistband of pants, that may be worn around their hip area for providing vestibular stimulation to the hip area of the user may alternatively be used.

Ankle stimulators 126A and 126B are shown as ankle bands including one or more vestibular stimulators incorporated therein for providing bone conduction stimulation to the ankle region of a wearer's body in response to receiving control information from controller 110. Ankle stimulators 126A, 126B may be incorporated in any article of clothing or apparatus that may be worn by a user of the wearable system 200. For example, ankle stimulators may be incorporated within an ankle-supporting bandage, socks, shoes, boots, or the portions of pants or leggings that cover the user's ankles.

The wearable components of the wearable system can be controlled separately to serve different therapeutic purposes. Although wearable system 200 is described herein as including two auditory stimulators (at the two ears) and six vestibular stimulators (head, hip, wrists, ankles), it should be appreciated that any number of auditory and vestibular stimulators may alternatively be used. In one embodiment, wearable system includes auditory stimulators, such as speakers in headphones, to provide air conduction stimulation to the user and wrist stimulators that provide bone conduction stimulation to the wrist area of the user. In other embodiments, the wearable system includes wearable pieces that perform auditory stimulation in combination with another set of vestibular stimulation components.

The inventors have recognized that pairing air conduction stimulation with bone conduction stimulation enhances auditory-vestibular integration. Accordingly, a system that includes headphones or some other auditory stimulation device in combination with a set of bone conduction wearable device components is important to provide effective therapy of sensory motor deficits. The wrist stimulators and ankle stimulators may, preferably, be worn in pairs, with each of the stimulators in the pair capable of being weighted in its application to increase the wearer's sense of directionality.

In addition to stimulators, wearable system 200 includes a plurality of sensors configured to sense aspects of the user as movement-based exercises are performed. Some sensors included in wearable system 200 may be configured to track the placement of, for example, the wearer's ankles, wrists, hip, and head during movements by the wearer of the system. The body alignment of the wearer of the wearable system provides data regarding the wearer's progress in posturing and alignment in various movement-based activities. Information regarding posture and alignment may be determined based on the relative positioning of each of the motion sensors in the wearable system. Motion detected with all or a subset of the motion sensors in the wearable system may be recorded through the trajectory of the movement made and the motion information may be transmitted back to controller 110 for storage, display, and/or processing on a computing device associated with controller 110. For example, the motion information recorded by each motion sensor may be displayed using a different color when viewed on the computing device.

In addition to motion sensors, wearable system 200 may be configured to include one or more sensors for sensing the sympathetic arousal of the wearer of the system during stimulation and/or performance of one or more movements. Examples of sympathetic arousal sensors include, but are not limited to, heart rate sensors, sweat sensors, pupil dilation sensors, and neurological monitoring sensors. In one implementation described in more detail below, a heart rate sensor is integrated with a wearable wrist or glove component of the wearable system. In another implementation, one or more sweat sensors may be integrated with a wearable component (e.g., a wearable glove component) of the wearable system to sense perspiration that reflects a level of sympathetic arousal of the wearer. Other types and placements of sympathetic arousal sensors may alternatively be used, and embodiments are not limited in this respect.

Some of the sensors in wearable system 200 may be integrated with wearable components of the system, whereas other sensors may be external to wearable components of the system. An example of external sensors that may be used with wearable system 200 are sensors included in a sensory mat 210. In some embodiments, sensory mat 210 is configured to provide input for the balance and weight distribution of the wearer of wearable system 200 during a movement-based activity. In one implementation, sensory mat 210 includes a plurality of sensors (e.g., a 3×3 grid of sensors) configured to sense a user's balance and weight distribution in different portions (e.g., quadrants) of the sensory mat. In some embodiments, the surface of the sensory mat 210 may be marked with identifiers to help the user orient to different axes while performing movements. Sensory mat 210 may be configured to allow disparities in the symmetry of movement to be determined as changes in the distribution of weight are tracked.

In some embodiments, one or more of the stimulators and sensors of the wearable system may be configured to be turned on or off as needed. Control of whether a particular component of the wearable system is on or off may be provided via one or more on/off switches located on a wearable component of the system. Alternatively, the controller may be configured to provide on/off control for individual components of the wearable system.

Figure 3:
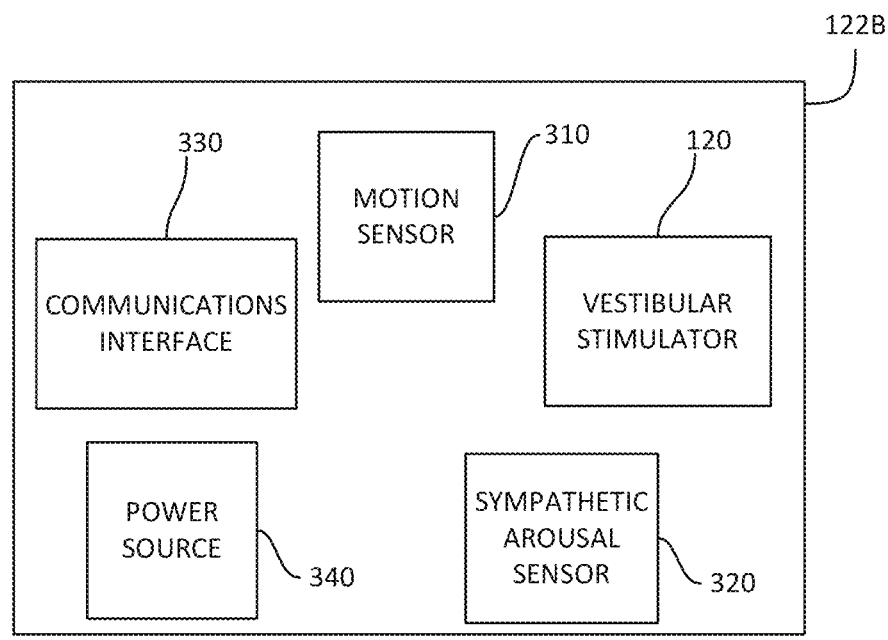
FIG. 3 shows a block diagram of a wearable component of a wearable system in accordance with some embodiments.

As discussed above, one or more of the wearable components of the wearable system may include, in addition to stimulation devices, one or more sensors, and a communications interface for communicating with controller 110 or other wearable or external components of the system. FIG. 3 schematically illustrates components included in wrist stimulator 122B that may be included in a wearable system in accordance with some embodiments. In addition to vestibular stimulator 120, wrist stimulator 122B includes a motion sensor 310 configured to track the position of the wearer's wrist during performance of movement activities and a sympathetic arousal sensor 320 (e.g., a heart rate sensor) configured to analyze the sympathetic arousal of the user during performance of movement activities. Wrist stimulator 122B further includes communications interface (e.g., a Bluetooth interface) configured to enable the wrist stimulator to receive control information from controller 110 and to transmit information determined from the motion sensor 310 and the heart rate sensor 320 to the controller 110. Wrist stimulator 112B further includes at least one power source 340 configured to provide operating power to one or more of vestibular stimulator 120, motion sensor 310, and heart rate sensor 320. In some embodiments, power source 340 may be implemented as a rechargeable or replaceable battery.

The motion sensors included in the wearable system needed to effectively gauge postural and alignment changes during movement-based activities may be determined based on the movements being performed. For example, if the activities being performed involve movement of the entire body, it may be preferable to include motion sensors on all six (or more) wearable pieces of the wearable system described above. Alternatively for activities that involve movements isolated in certain parts of the body, a smaller set of motion sensors including, but not limited, to a single motion sensor may be used to track motion in the part(s) of the body involved in the movements. Because many individuals struggle with movement overflow, or the inability to isolate movement to specific parts of their body, it may be advantageous in some situations to use a larger set of motion sensors distributed on parts of the body other than the body part implicated in a particular movement or activity to gauge the presence of such movement overflow in the other parts of the body.

Wearable components of wearable system 200 may include stimulators only, a combination of stimulators and sensors, or sensors only, as aspects of the present disclosure are not limited in this respect. For wearable components that include only sensors or only stimulators, it should be appreciated that unidirectional communication functionality with the controller (e.g., from controller 110 to the wearable component or vice versa) may be used rather than the bidirectional communication discussed above in connection with the exemplary wrist stimulator 122B shown in FIG. 3.

Figure 4:
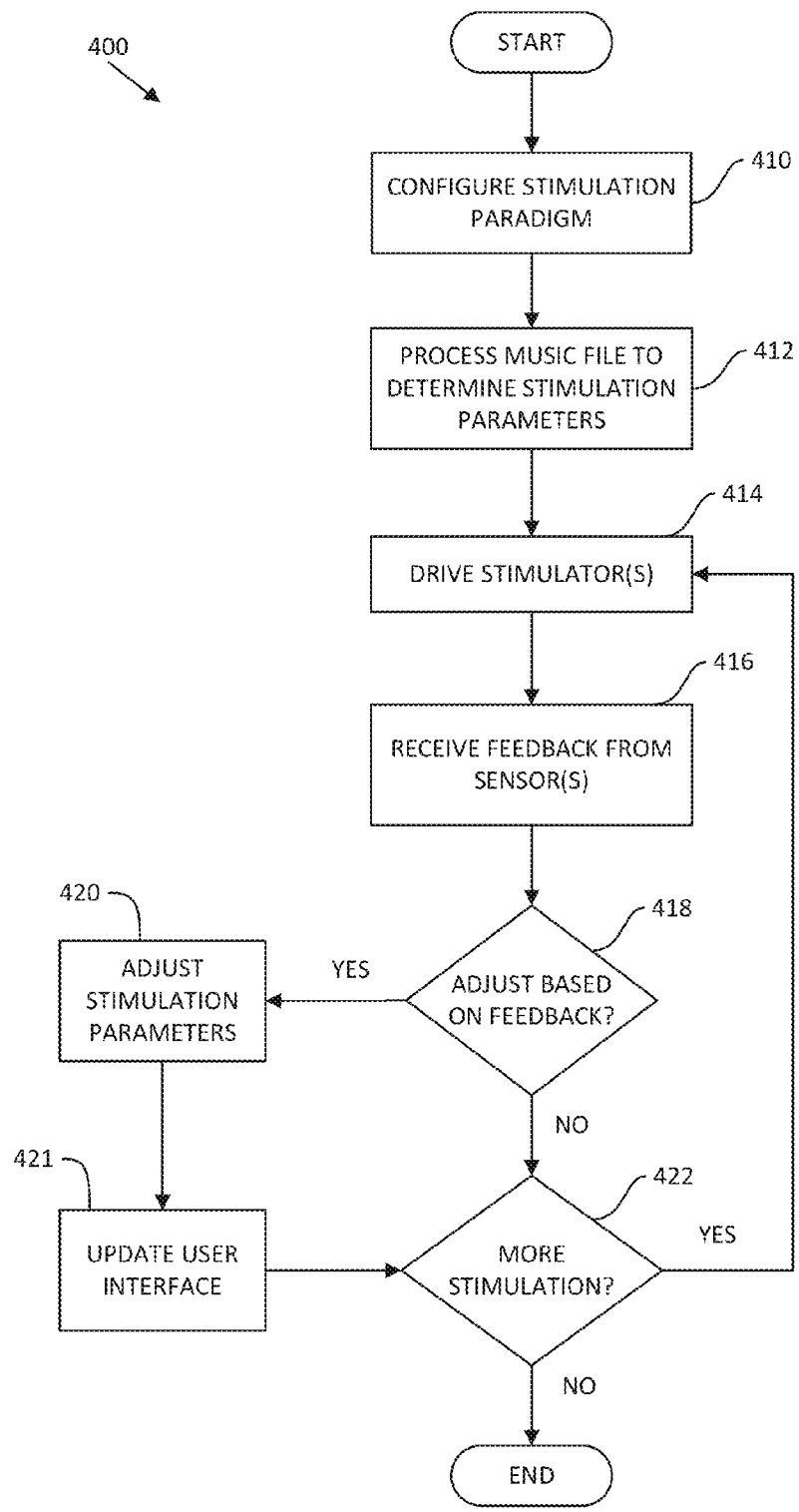
FIG. 4 is a flow chart of a process for determining stimulation parameters in a wearable system in accordance with some embodiments.

FIG. 4 shows a flow chart of a process for performing stimulation in accordance with some embodiments. In act 410, a stimulation paradigm is configured. The stimulation paradigm describes how an audio file (e.g., a music file) is processed by the controller of the wearable system to control the stimulators in the system based on the content of the recorded audio. In one aspect, therapeutic effects in response to the stimulation are made possible with full spectrum music that preserves the full spectrum of sounds rather than simply preserving tonal balance in the music files being processed.

In some embodiments, the stimulation paradigm may be configured based on one or more characteristics of the user of the wearable system. For example, the stimulation paradigm may be configured based on a diagnosis of the user, demographic characteristics (e.g., age) of the user, the user's performance on one or more assessments, and/or the user's history of performance performing one or more movement-based activities while wearing the wearable system. Configuring the stimulation paradigm may include, but is not limited to, selecting the wearable stimulators to be worn/activated and selecting stimulation parameters such as amplification and timing. In some embodiments, higher frequencies determined from a processed music file are amplified for presentation using air conduction via auditory stimulators and lower frequencies determined from the processed music file are amplified for presentation using bone conduction stimulation via one or more vestibular stimulators, examples of which are described above.

When multiple vestibular stimulators are used to provide bone conduction stimulation, the amplification applied to low frequency components of music may differ across the multiple vestibular stimulators. Providing different levels of amplification across multiple vestibular stimulators allows the bone conduction stimulation to have different therapeutic effects. In one implementation, the balance of bone conduction amplification may be adjusted across multiple vestibular stimulators that are arranged vertically on the wearer's body. For example, the balance of the bone conduction amplification may range from equal vibrations across all wearable vestibular stimulators to an amplification distribution stronger (e.g., twice as strong) at the wrist and ankles than at the head and waist, thereby more closely mirroring how human bodies process sounds during natural human development. In another implementation, the balance of bone conduction may be adjusted across multiple vestibular stimulators that are arranged laterally (e.g., left-right balance) on the wearer's body. For example, balancing bone conduction stimulation laterally by providing more amplification on the right side or the left side of the body may imitate sound transmission from different sources in space to increase and enhance the wearer's spatial awareness. In yet a further implementation, the balance of bone conduction amplification may be adjusted across multiple vestibular stimulators arranged in both vertical and lateral directions on the wearer's body.

In some embodiments, the balance of the amplification of air conduction stimuli presented using auditory stimulators may also be adjusted such that the amplification will be stronger on the right side or the left side. Amplification adjustments to individual stimulators may be coordinated by a controller implemented as an application on a computing device (e.g., a smartphone), an example of which is described above.

In some embodiments the stimulation paradigm is selected and/or configured automatically based on the user's prior use of the wearable system. Alternatively, the stimulation paradigm, or aspects of the stimulation paradigm may be manually selected by a user via a user interface of a control application provided on a computing device. An example of portions of a user interface that may be used in accordance with some embodiments to select and/or configure a stimulation paradigm are described in more detail below. In some embodiments, configuring a stimulation paradigm includes choosing an audio file (e.g., a music file) to play on the computing device. The selected file is then processed as the file is being played to determine stimulation parameters as discussed in more detail below.

After the stimulation paradigm has been configured, the process 400 proceeds to act 412, where a music file is processed to determine stimulation parameters to transmit to the wearable stimulator components of the wearable system. As described briefly above, in some embodiments, high frequencies in music being played may be amplified and presented using air conduction via one or more auditory stimulators, whereas low frequencies may be amplified and presented using bone conduction via one or more vestibular stimulators. To determine how to control the individual wearable stimulator components of the wearable system, the music file being played is processed to determine the high frequency portions and low frequency portions for driving the appropriate stimulators in accordance with the configured stimulation paradigm.

Following processing of the music file to determine the stimulation parameters, the process 400 proceeds to act 414, where control information based on the stimulation parameters is sent from the controller to each of the wearable stimulator components of the wearable system being controlled. The control information may be sent to each of the individually controllable wearable components of the system using Bluetooth communication or any other wired or wireless communication technique.

Prior to beginning execution of the configured stimulation paradigm, the wearable system may be configured to capture one or more baseline measurements from one or more sensors in the wearable system. As described above, the wearable system may include one or more sensors configured to sense aspects of the user as movement-based exercises are performed and while the stimulation is being provided. Baseline measurements may be recorded for motion sensors configured to determine postural alignment of the user and for sensors configured to determine sympathetic arousal. In one implementation, the baseline measurements are recorded while the user moves through a series of positions and exercises such as lying down in a corpse pose on the sensory mat, sitting on the sensory mat, standing on the sensory mat, walking for 50 meters, and running for 100 meters. Data recorded by the individual sensors may be transferred back to the controller to set baseline sensor levels. The baseline sensor levels may be used during performance of the activities as a reference for detecting deviations indicating, for example, a heightened sympathetic arousal.

Following establishment of the baseline sensor levels and while stimulation is occurring, the process 400 proceeds to act 416, where feedback information is received by the controller from one or more sensors included in the wearable system. At least some of the sensors may be integrated with the wearable stimulator components of the wireless system, whereas other sensors (e.g., in a sensory mat) may be separate from the wearable pieces of the wearable system, but which are nonetheless capable of tracking information (e.g., posture information) about the user as the user performs movement-based activities.

The process then proceeds to act 418, where it is determined based, at least in part, on the received feedback whether to adjust one or more of the stimulation parameters for the stimulation paradigm. Adjusting one or more of the stimulation parameters includes, but is not limited to, modifying the amplification of the stimulation for one or more of the stimulators in the wearable system and selecting a different set of stimulators to use for stimulation. If it is determined based on the feedback that the stimulation parameters should be adjusted, the process proceeds to act 420, where the stimulation parameter(s) are adjusted and updated control information is transmitted to some or all of the wearable stimulator components of the wearable system. The process then proceeds to act 421, where the user interface provided by the controller of the system is updated to reflect the adjusted stimulation parameters. By updating the user interface in response to changes in simulation as a result of sympathetic arousal feedback, the wearer of the system is provided with up-to-date information about the current intensity of stimulation. If it is determined in act 418 that no adjustments to the stimulation parameters are needed, the process proceeds to act 422, where it is determined whether further stimulation is required by the selected stimulation paradigm. If it is determined in act 422 that more stimulation is required, the process returns to act 414, where further stimulation is provided. If it is determined in act 422 that stimulation is no longer required, the process 400 ends.

Figure 5:
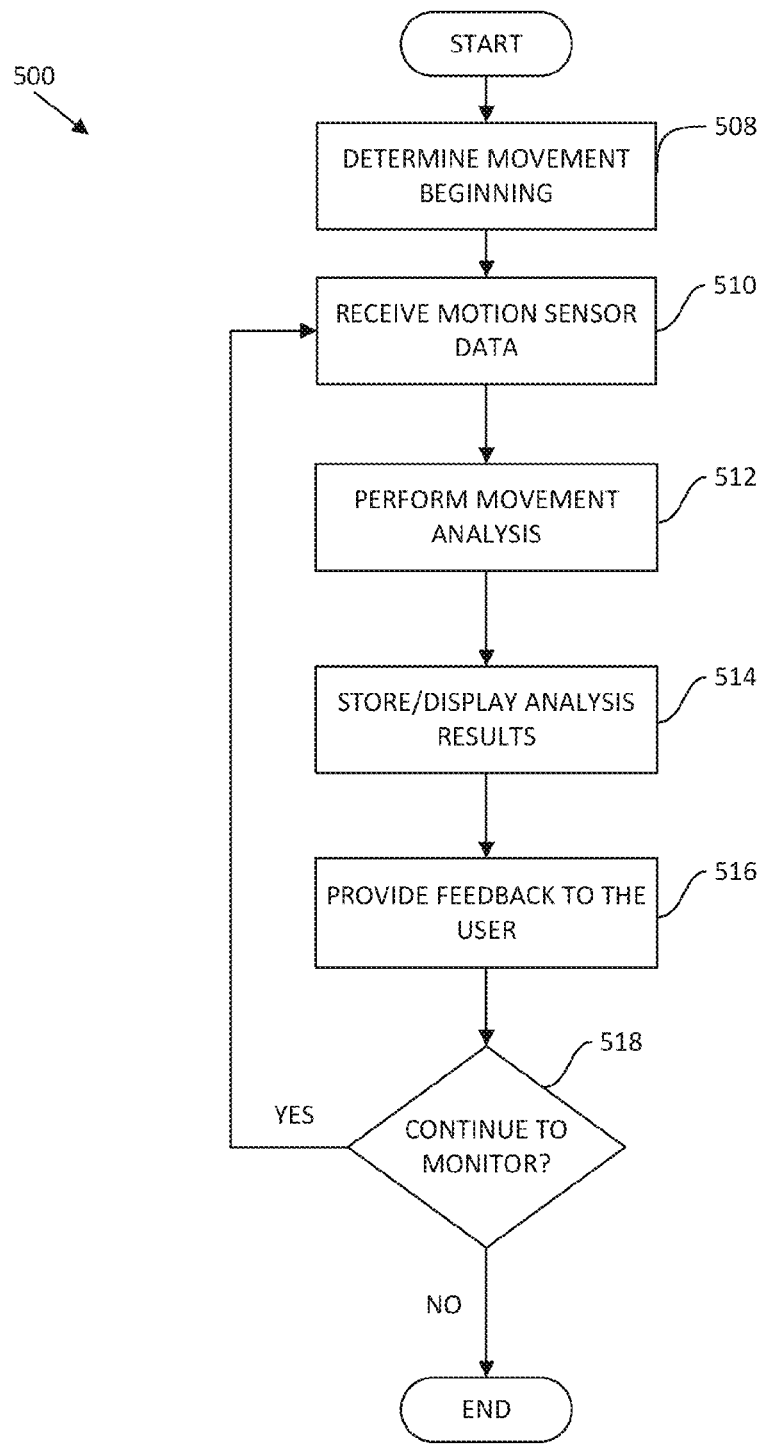
FIG. 5 is a flow chart of a process for tracking motion of a user wearing components of a wearable system in accordance with some embodiments.

FIG. 5 shows a flow chart of a process 500 for tracking motion of a user during performance of movement-based activities in accordance with some embodiments. In act 508, the controller determines that a movement is beginning or has begun. This determination may be made in any suitable way. In some embodiments, the wearer of the device may manually specify (e.g., through an interaction with a user interface of a control application) that a particular movement is beginning or has begun. In other embodiments, the determination that a particular movement is beginning or has begun may made, at least in part, automatically by the controller based on motion sensor data received by the controller. In response to determining that a particular movement is beginning or has begun, the controller may determine a desired movement pattern for the particular movement being performed by the wearer of the system. A comparison of actual movements sensed by the system and the desired movement pattern for the particular movement may be used to provide feedback to the user, as described in more detail below.

After the controller has determined that a particular movement has begun, process 500 proceeds to act 510, where motion sensor data collected during performance of the particular movement is received by the controller in the wearable system from one or more motion sensors. In some embodiments, each of the wearable components of the wearable system includes a motion sensor for tracking the motion of a respective body part with which the wearable component is associated. Inclusion of more motion sensors in the wearable system enables the capture of more information enabling the system to analyze a user's movements in more complex ways. Some embodiments include fewer motion sensors to reduce the cost of the wearable system, particularly if the wearable system is designed for use with movement-based activities that do not involve motion of the entire body.

After motion sensor data is received by the controller, the process 500 proceeds to act 512, where the controller performs a movement analysis based on the received motion sensor data and a desired movement pattern for the particular movement being performed. In some embodiments, the movement analysis incorporates and synthesizes motion sensor data captured from multiple motion sensors included in the wearable system. In other embodiments, the movement analysis analyzes motion sensor data from each motion sensor separately, and tracks deviations from a desired motion. In yet other embodiments, both synthesized movement analysis and movement analysis based on individual sensors are performed. The process 500 then proceeds to act 514 where the analysis results are stored and/or displayed by the computing device that includes the controller. The analysis results may be stored locally on the computing device, stored on a local storage device in communication with the computing device, or stored on a remote storage device (e.g., in the cloud) in communication with the computing device via one or more networks. In some embodiments, at least some of the results of the movement analysis may be displayed on the computing device or on another device in communication with the computing device.

The process 500 then proceeds to act 516, where feedback is provided to the user based, at least in part, on the movement analysis. The feedback may be provided to the user in any suitable way. In one implementation, feedback may be provided through the adjustment of the stimulation parameters to encourage the user to perform movements differently. For example, if the movement analysis determines that the posture of the user is weighted more on the left side than the right side, the stimulation parameters may be adjusted to increase the amplification of the stimulation provided to the left side to encourage the user to correct the posture to a more balanced position. In some embodiments, feedback may be provided to the user through auditory or visual presentation of a signal detectable by the user. For example, the controller may instruct one or more of the auditory stimulators to output an audio signal to provide the feedback. The audio signal may comprise an increase or decrease in the amplification of the music presented to the auditory stimulator(s) or the audio signal may comprise a different auditory stimulus (e.g., one or more tones) to be presented as feedback. Feedback may be presented to the user visually in some embodiments by displaying on a user interface of the computing device, a plot or other representation of the sensed movements.

An example of feedback that may be provided in accordance with some embodiments is crossing center movement feedback. In this type of feedback, when the user's right arm or right leg crosses the center to the left side of the body, as defined by the axis drawn from connecting a motion sensor at the top of the head to a motion sensor at the middle of the hips, or the left arm or left leg crosses the center to the right side of the body, as defined by the axis drawn from connecting motion sensor at the top of the head to a motion sensor at the middle of the hips, the controller will determine and record an indication that that the center has been crossed by the movement. The indication of the center crossing may also be displayed on a user interface provided by the control application.

Another example of feedback that may be provided in accordance with some embodiments relates to assessment of symmetry in movement. In this type of feedback, changes in posture due to movement are recorded throughout a movement session, and the changes in posture are analyzed in discrete segments for the symmetry of movement. A full iteration of a movement pattern may be captured and the movements made, and subsequent changes in weight distributions, compared to highlight the ways in which asymmetry is present in the movement. Information about the user's posture may be captured in some embodiments by a plurality of motion sensors incorporated into a sensory mat and/or motion sensors integrated with wearable components of the wearable system. The results of the symmetry assessment may be displayed on a user interface provided by the control application.

Yet another example of feedback that may be provided in accordance with some embodiments relates to movement and motion feedback. In some embodiments, movements and weight distributions are recorded by motion sensors incorporated in at least some of the wearable components of the wearable system and the sensory mat, and the tracked movement data may be displayed on a user interface of the control application. The motions sensed by each motion sensor may be displayed as lines of motion that follow each movement via the motion sensor, and the weight distribution sensed by the sensors in the sensory mat may be recorded as colors indicating different forces that are exerted upon the sensory mat.

After feedback is provided to the user, the process 500 proceeds to act 518, where it is determined whether to continue monitoring movements by the motion sensors of the wearable system. If it is determined to continue monitoring movements, the process returns to act 510 where additional motion sensor data is received and processed. Otherwise, the process 500 ends.

Figure 6:
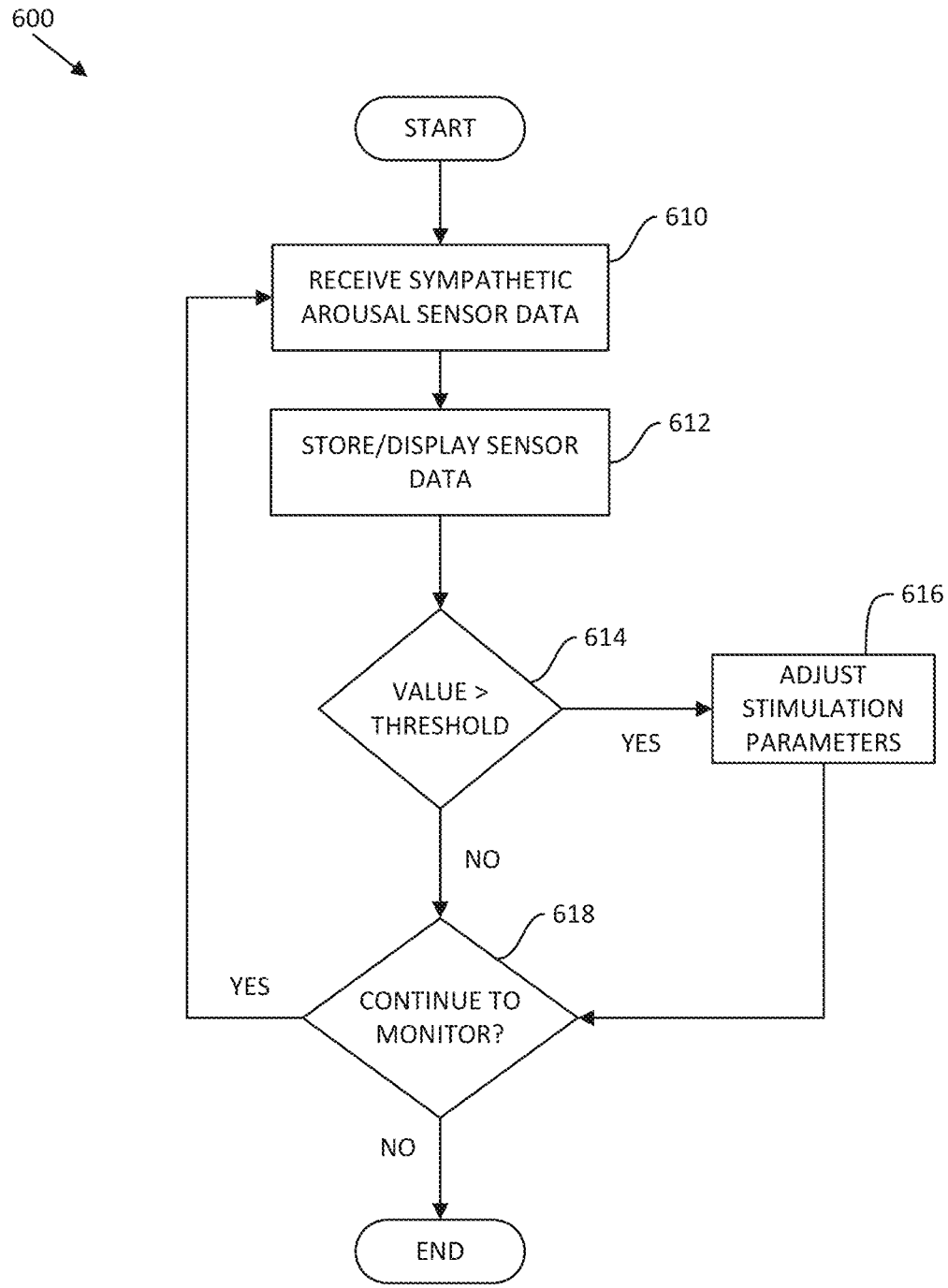
FIG. 6 is a flow chart of process for tracking heart rate information of a user wearing components of a wearable system in accordance with some embodiments.

FIG. 6 shows a flow chart of a process 600 for processing feedback from a sympathetic arousal sensor in accordance with some embodiments. In act 610, sympathetic arousal sensor data is received by the controller, which may be implemented on a computing device, such as a smartphone. Sympathetic arousal sensor data (e.g., heart rate sensor data) may be sensed by one or more sensors in the wearable system. In the example of FIG. 3, the sympathetic arousal sensor is integrated with a wrist stimulator wearable component of the wearable system. However, sympathetic arousal sensors in accordance with some embodiments may be located at any location on the body capable of sensing sympathetic arousal of the user, and may be integrated with or provided separately from wearable components that include stimulators. Process 600 then proceeds to act 612, where the sympathetic arousal sensor data is stored and/or displayed by the computing device.

The process then proceeds to act 614, where it is determined whether the sensed sympathetic arousal is greater than a threshold value. Any suitable threshold value may be used, and aspects of the present disclosure are not limited in this respect. In some embodiments, the threshold value is set based, at least in part, on a baseline value recorded prior to the movement session. For example, the threshold value may be set at 150% of the baseline sympathetic arousal value. In some embodiments, the threshold value is set based, at least in part, on body posturing of the wearer determined based on motion sensor data. For example, if the wearer of the system is lying down, the threshold may be set to 150% of the baseline sympathetic arousal value determined when the wearer was lying down. By contrast, if the wearer of the system is standing up, the threshold may be set to 150% of the baseline sympathetic arousal value determined when the wearer was standing.

When it is determined that the sympathetic arousal value is greater than the threshold, the process proceeds to act 616, where one or more stimulation parameters are adjusted. In the event of strong sympathetic arousal as measured through elevated sympathetic arousal beyond an amount above the baseline sympathetic arousal value, the device may automatically alert the wearer of the wearable system of the heightened sympathetic arousal with an auditory stimulus such as three, high frequency, audible beeps through the headphones for the wearer. Additionally or alternatively, feedback may be provided my changing the vestibular sensor parameters. For example, the amplification of the bone conduction stimulation may be decreased by half. When the elevated sympathetic arousal value equals or exceeds a particular threshold (e.g., 150% of the baseline sympathetic arousal value), the music presented through the auditory stimulator(s) may automatically stop playing to alert the user of the elevated sympathetic arousal.

The process 600 then proceeds to act 618, where it is determined whether there should be additional sympathetic arousal monitoring. If it is determined that additional sympathetic arousal monitoring is needed, the process returns to act 610, where monitoring of the user's sympathetic arousal continues. Otherwise, the process 600 ends.

In some embodiments, operation of the wearable system is controlled using at least one controller (e.g., a computer processor) programmed to execute an application installed on a computing device, such as a smartphone. FIGS. 7A-7D show examples of portions of a user interface that may be presented by the control application on a display in accordance with some embodiments.

In some embodiments, the control application is user specific and requires a user to log in using user credentials. After successful log in, the user may be presented with an option to select one of a plurality of pages, examples of which are described in more detail below. In some embodiments, each of the pages includes one or more user interface elements that enables the user to navigate to other pages of the of the control application. FIGS. 7A-7D, described in more detail below, show the navigation elements as user interface buttons with which a user may interact to navigate to a different page of the application. However, it should be appreciated that navigation to pages of the application may be implemented using any suitable user interface element or technique. It should be appreciated that the portions of a user interface shown in FIGS. 7A-7D are provided merely for illustration and do not limit aspects of the present disclosure.

Figure 7A:
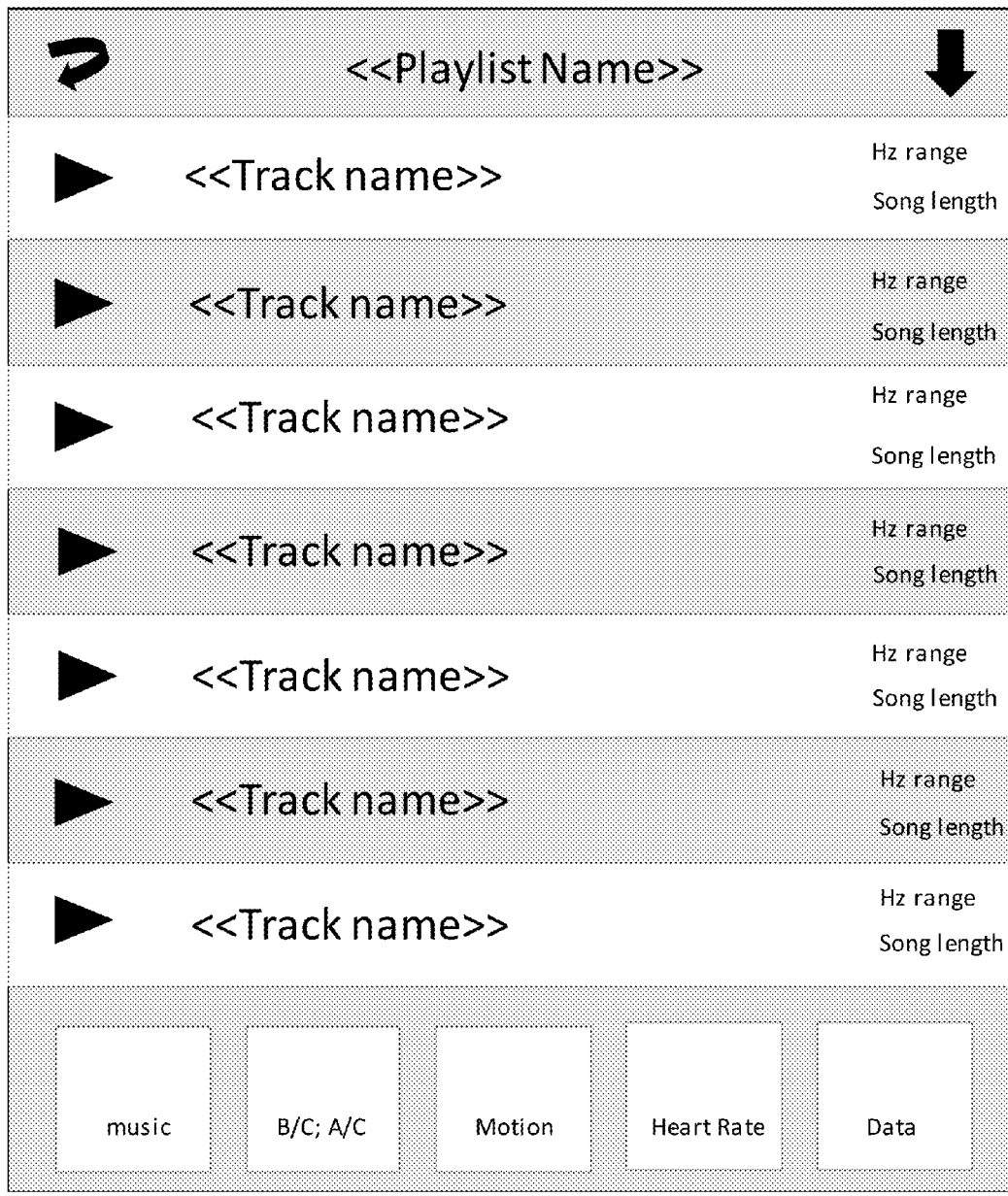
FIGS. 7A-7D illustrate portions of a user interface that may be presented by a controller of a wearable computer system in accordance with some embodiments.

FIG. 7A shows an example of a music selection page that may be included as a portion of a user interface in accordance with some embodiments. The music selection page may be configured to enable the user to upload music, organize the music, and select music to play, pause, or skip during operation of the wearable system.

Figure 7B:
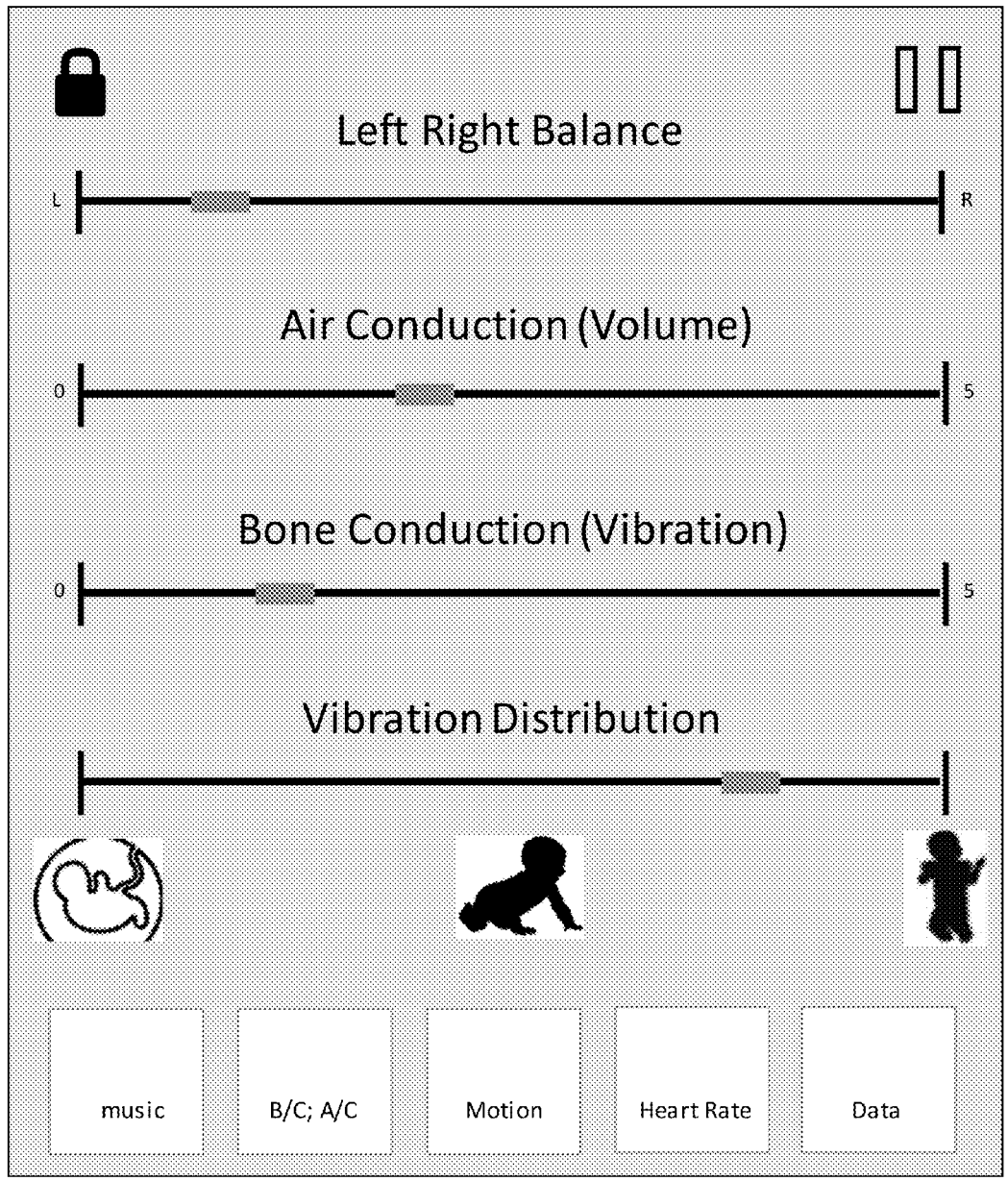

FIG. 7B shows an example of a stimulation settings page that may be included as a portion of a user interface in accordance with some embodiments. The stimulation settings page as shown includes four bars. The first bar allows the user to adjust the left/right balance of sounds transmitted via air conduction through the headphones. The second bar allows the user to adjust air conduction, or the amplification of sounds via air waves through the headphones, to be used as a volume control. The third bar allows the user to adjust the amplification of sounds via bone conduction, via vibrations, through one or more of the vestibular stimulators in the wearable components of the device. The fourth bar allows the user to adjust the balance in the vibrations across the vestibular stimulators, examples of which are described above.

Figure 7C:
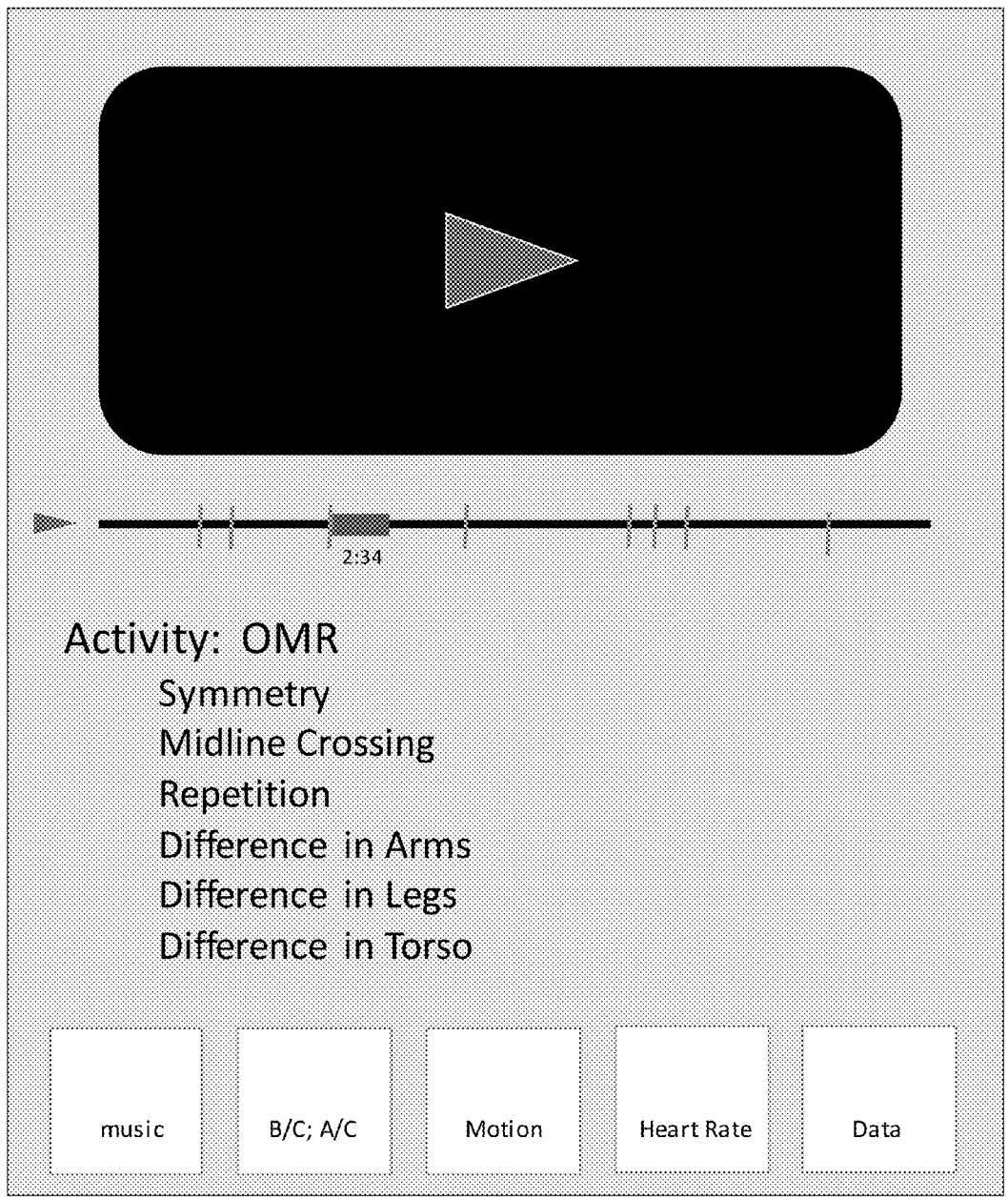

FIG. 7C shows an example of a movement analysis page that may be included as a portion of a user interface in accordance with some embodiments. The movement analysis page may include options for one or more of enabling the user to begin the movement session tracking, replaying motions performed in segments of previous sessions, displaying the sensed weight distribution throughout the session, comparing motions in prior sessions to baseline, tracking the number of times the user crossed their midline vertically, laterally, or in front and back, tracking the number of iterations of movement patterns that are completed, tracking the congruency of movements by the arms or by the legs, or providing any other capability to control tracking of movements by the motion sensors in the wearable system or to display the results based on the feedback received by the control application from the motion sensors.

Figure 7D:
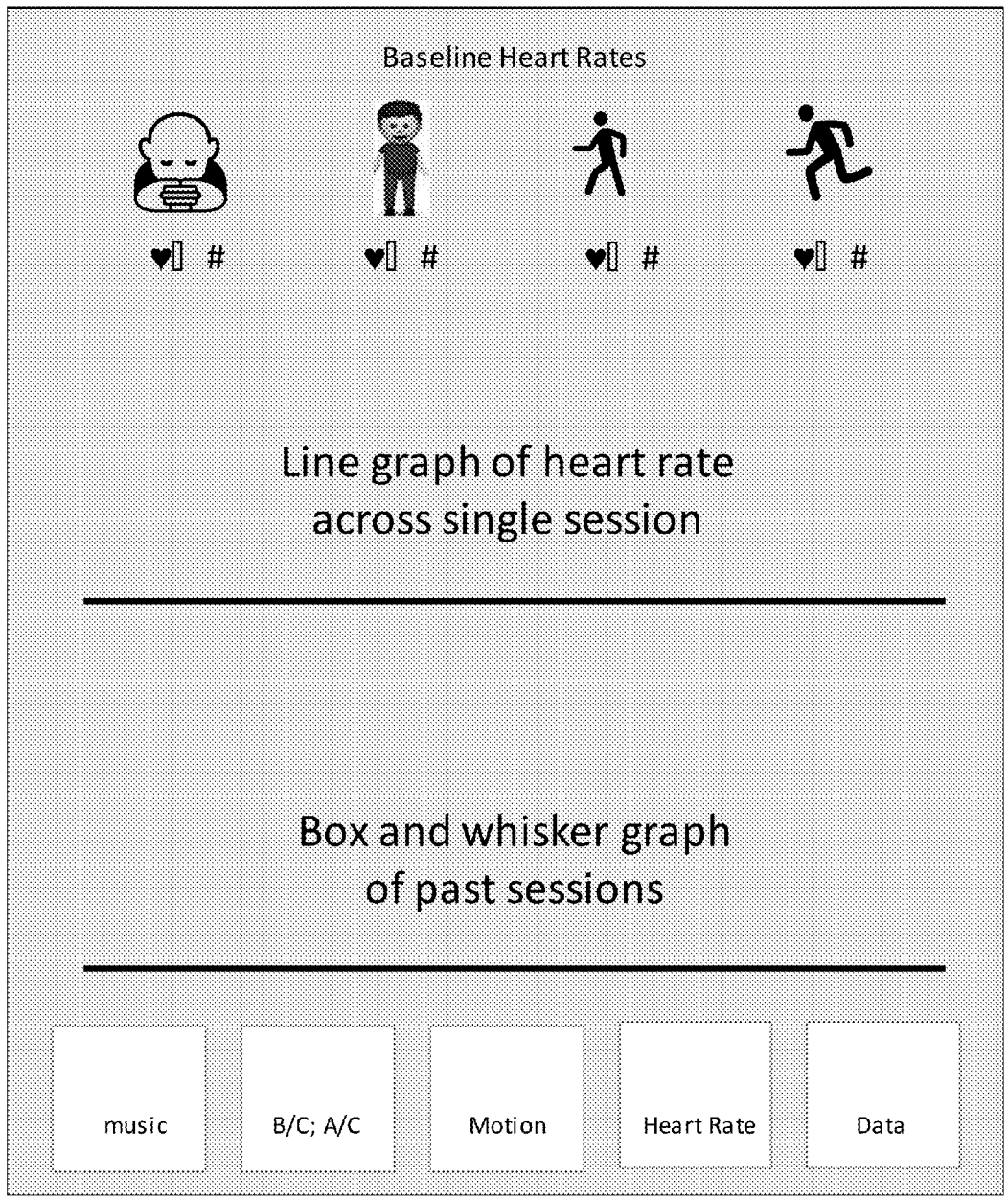

FIG. 7D shows an example of a sympathetic arousal analysis page that may be included as a portion of a user interface in accordance with some embodiments. The sympathetic arousal analysis page as shown provides the baseline values of the user in different states of sympathetic arousal. The sympathetic arousal data received from sympathetic arousal sensors may be stored and data on the user's sympathetic arousal in prior sessions may be viewed across different periods of time. As shown, the baseline sympathetic arousal data may be displayed in a static display with the ability to add a new baseline if desired. Data on the user's sympathetic arousal in previous sessions may also be displayed graphically. For example, a display of sympathetic arousal data from the past session or multiple past sessions (e.g., the past ten recorded sessions) may be displayed. In the implementation shown, sympathetic arousal (e.g., heart rate) tracked over a single session may be shown as a line graph on the sympathetic arousal analysis page. Alternatively, a display of sympathetic arousal data for a single session may comprise a box and whisker line graph of ten minute increments. As shown, a display for multiple previous sessions may comprise a box and whisker line graph of sympathetic arousal for each of multiple previous sessions.

The above-described embodiments can be implemented in any of numerous ways. For example, the embodiments may be implemented using hardware, software or a combination thereof. When implemented in software, the software code can be executed on any suitable processor or collection of processors, whether provided in a single computer or distributed among multiple computers. It should be appreciated that any component or collection of components that perform the functions described above can be generically considered as one or more controllers that control the above-discussed functions.

In this respect, it should be appreciated that one implementation of the techniques described herein comprises at least one non-transitory computer-readable storage medium (e.g., a computer memory, a USB drive, a flash memory, a compact disk, a tape, etc.) encoded with a computer program (i.e., a plurality of instructions) that, when executed on a processor, performs the above-discussed functions. The computer-readable storage medium can be transportable such that the program stored thereon can be loaded onto any computer resource to implement the aspects of embodiments discussed herein.

Various techniques described herein may be used alone, in combination, or in a variety of arrangements not specifically discussed in the embodiments described in the foregoing and are therefore not limited in their application to the details and arrangement of components set forth in the foregoing description or illustrated in the drawings. For example, aspects described in one embodiment may be combined in any manner with aspects described in other embodiments.

Also, embodiments may be implemented as one or more methods, of which an example has been provided. The acts performed as part of the method(s) may be ordered in any suitable way. Accordingly, embodiments may be constructed in which acts are performed in an order different than illustrated, which may include performing some acts simultaneously, even though shown as sequential acts in illustrative embodiments.

Use of ordinal terms such as "first," "second," "third," etc., in the claims to modify a claim element does not by itself connote any priority, precedence, or order of one claim element over another or the temporal order in which acts of a method are performed. Such terms are used merely as labels to distinguish one claim element having a certain name from another element having a same name (but for use of the ordinal term).

The phraseology and terminology used herein is for the purpose of description and should not be regarded as limiting. The use of "including", "comprising," "having," "containing", "involving", and variations thereof, is meant to encompass the items listed thereafter and additional items.

Having described several embodiments in detail, various modifications and improvements will readily occur to those skilled in the art. Accordingly, the foregoing description is by way of example only, and is not intended as limiting.

What is claimed is:

1. A wearable system, comprising:
    a plurality of wearable components; and
    a controller configured to communicate with each of the plurality of wearable components, wherein the plurality of wearable components include:
        at least one auditory stimulator configured to provide air conduction stimulation to a user in response to receiving first control information from the controller, wherein the first control information includes amplified music information determined based on high-frequency content of music processed by the controller;
        a plurality of vestibular stimulators configured to provide bone conduction stimulation to the user in response to receiving second control information from the controller, wherein the second control information includes amplification information determined based on low frequency content of the music processed by the controller, wherein a first vestibular stimulator of the plurality of vestibular stimulators is integrated into a first wearable component of the wearable system configured to be worn in contact with a first portion of the user's body and a second vestibular stimulator of the plurality of vestibular stimulators is integrated into a second wearable component of the wearable system configured to be worn in contact with a second portion of the user's body;
        at least one motion sensor integrated with the first wearable component and configured to sense motion information of the first portion of the user's body and provide the sensed motion information to the controller; and
        at least one sympathetic arousal sensor configured to sense sympathetic arousal information of the user during stimulation by the plurality of vestibular stimulators and to provide the sensed sympathetic arousal information to the controller;

wherein the controller is further configured to adjust the first control information and/or the second control information based, at least in part, on the sensed motion information and/or the sensed sympathetic arousal information.

2. The wearable system of claim 1, wherein the at least one sympathetic arousal sensor comprises a heart rate sensor configured to measure a heart rate of the user.

3. The wearable system of claim 1, wherein the plurality of vestibular stimulators comprises a head vestibular stimulator, a pair of wrist vestibular stimulators, a hip vestibular stimulator, and a pair of ankle vestibular stimulators.

4. The wearable system of claim 1, wherein the at least one sympathetic arousal sensor is integrated with the first wearable component of the wearable system.

5. The wearable system of claim 4, wherein the first wearable component comprises a wristband or a glove.

6. The wearable system of claim 1, wherein the amplification information included in the second control information includes first amplification information for controlling a first amplification of a bone conduction stimulus output by the first vestibular stimulator and second amplification information for controlling a second amplification of a bone conduction stimulus output by the second vestibular stimulator, wherein the first amplification and the second amplification are different.

7. The wearable system of claim 1, wherein the controller is further configured to instruct the at least one sympathetic arousal sensor to sense baseline sympathetic arousal information of the user prior to stimulation by the plurality of vestibular stimulators and to provide the sensed baseline sympathetic arousal information to the controller.

8. The wearable system of claim 7, wherein adjusting the first control information and/or the second control information based, at least in part, on the sensed sympathetic arousal information comprises:

comparing the sensed sympathetic arousal information to a threshold value set based, at least in part, on the baseline sympathetic arousal information; and adjusting the first control information and/or the second control information when the sensed sympathetic arousal information is above the threshold value.

9. The wearable system of claim 1, wherein the at least one auditory stimulator, the first vestibular stimulator, and the second vestibular stimulator are configured to output stimulation to the user simultaneously.

10. The wearable system of claim 1, wherein the controller is further configured to:

determine a posture of the user based, at least in part, on the sensed motion information received from the at least one motion sensor; and wherein adjusting the first control information and/or the second control information comprises adjusting the first control information and/or the second control information to indicate to the user the determined posture.

11. The wearable system of claim 10, wherein adjusting the first control information and/or the second control information to indicate to the user the determined posture comprises instructing the at least one auditory stimulator to output one or more tones on a left side of the user or a right side of the user or instructing at least one of the plurality of vestibular sensors to increase an amplification of a bone conduction stimulus on the left side of the user or the right side of the user.

12. The wearable system of claim 11, wherein the adjusting the first control information and/or the second control information to indicate to the user the determined posture comprises instructing at least one of the plurality of vestibular sensors to increase an amplification of a bone conduction stimulus on the left side of the user or the right side of the user without changing a timing of the bone conduction stimulus determined based on the low frequency content of the music.

13. The wearable system of claim 1, further comprising a sensory mat including a plurality of motion sensors that detect a weight distribution of the user, wherein the plurality of sensors are configured to transmit weight distribution information to the controller.

14. The wearable system of claim 13, wherein the controller is further configured to adjust the first control information and/or the second control information based, at least in part, on the weight distribution information received from the plurality of sensors included in the sensory mat.

15. A method of controlling a wearable system including a controller and a plurality of wearable components in communication with the controller, the plurality of wearable components including at least one auditory stimulator, a plurality of vestibular stimulators, at least one motion sensor, and at least one sympathetic arousal sensor, the method comprising:

performing, by the controller, a frequency analysis of music to determine high frequency content and low frequency content of the music;

receiving, by the at least one auditory stimulator, first control information from the controller, wherein the first control information is based on the determined high frequency content of the music;

providing, by the at least one auditory stimulator, air conduction stimulation to a user based, at least in part, on the first control information;

receiving, by the plurality of vestibular stimulators, second control information from the controller, wherein the second control information is based on the determined low frequency content of the music;

providing, by the plurality of vestibular stimulators, bone conduction stimulation to the user based, at least in part, on the second control information;

sensing, by the at least one motion sensor, motion information of a portion of the user's body;

transferring the sensed motion information from the at least one motion sensor to the controller;

sensing, by the at least one sympathetic arousal sensor, sympathetic arousal information of the user during stimulation by the plurality of vestibular stimulators;

transferring the sensed sympathetic arousal information from the at least one sympathetic arousal sensor to the controller; and adjusting, by the controller, the first control information and/or the second control information based, at least in part, on the sensed motion information and/or the sensed sympathetic arousal information.

16. The method of claim 15, wherein providing, by the plurality of vestibular stimulators, bone conduction stimulation to the user based, at least in part, on the second control information comprises:

controlling a first amplification of a bone conduction stimulus output by a first vestibular stimulator of the plurality of vestibular stimulators; and controlling a second amplification of a bone conduction stimulus output by a second vestibular stimulator of the plurality of vestibular stimulators;

wherein the first amplification and the second amplification are different.

17. A non-transitory computer readable medium encoded with a plurality of instructions that, when executed by at least one computer processor perform a method, the method comprising:
performing a frequency analysis of music to determine high frequency content and low frequency content of the music;
sending based on the determined high frequency content of the music, first control information to at least one auditory stimulator configured to provide air conduction stimulation;
sending, based on the determined low frequency content of the music, second control information to each of a plurality of vestibular stimulators configured to provide bone conduction stimulation;
receiving motion information of a portion of a user's body sensed by at least one motion sensor;
receiving sympathetic arousal information of a user sensed by at least one sympathetic arousal sensor; and
adjusting the first control information and/or the second control information based, at least in part, on the received motion information and/or the received sympathetic arousal information.

18. The non-transitory computer readable medium of claim 17, wherein sending, based on the low frequency content of the music, second control information to each of a plurality of vestibular stimulators configured to provide bone conduction stimulation comprises:
sending first bone conduction amplification information to a first vestibular stimulator of the plurality of vestibular stimulators instructing the first vestibular stimulator to provide bone conduction stimulation at a first amplification; and
sending second bone conduction amplification information to a second vestibular stimulator of the plurality of vestibular stimulators instructing the second vestibular stimulator to provide bone conduction stimulation at a second amplification;
wherein the first amplification and the second amplification are different.

* * * * *